(12) United States Patent
Ezra

(10) Patent No.: US 11,865,537 B2
(45) Date of Patent: Jan. 9, 2024

(54) PORTABLE DIGITAL DIAGNOSTIC DEVICE

(71) Applicant: E.F.A. ENGINEERING FOR ALL LTD., Yokneam (IL)

(72) Inventor: Yoel Ezra, Pardes-Hana Karkur (IL)

(73) Assignee: E.F.A. Engineering For All Ltd., Yokneam (IL)

( * ) Notice: Subject to any disclaimer, the term of this patent is extended or adjusted under 35 U.S.C. 154(b) by 1010 days.

(21) Appl. No.: 16/483,775

(22) PCT Filed: Feb. 6, 2018

(86) PCT No.: PCT/IL2018/050132
§ 371 (c)(1),
(2) Date: Aug. 6, 2019

(87) PCT Pub. No.: WO2018/142415
PCT Pub. Date: Aug. 9, 2018

(65) Prior Publication Data
US 2020/0023359 A1 Jan. 23, 2020

Related U.S. Application Data

(60) Provisional application No. 62/454,933, filed on Feb. 6, 2017.

(51) Int. Cl.
*B01L 3/00* (2006.01)
*A61B 5/1455* (2006.01)
(Continued)

(52) U.S. Cl.
CPC ...... *B01L 3/502715* (2013.01); *A61B 5/1455* (2013.01); *A61B 5/1468* (2013.01);
(Continued)

(58) Field of Classification Search
CPC .......... B01L 3/502715; B01L 3/50273; B01L 3/505; B01L 2300/0822; B01L 2300/0874;
(Continued)

(56) References Cited

U.S. PATENT DOCUMENTS 5,051,237 A 9/1991 Grenner et al.
5,073,857 A * 12/1991 Peters .................. G06T 7/0012
382/270

(Continued)

FOREIGN PATENT DOCUMENTS

CN 103969262 A 8/2014
CN 106324064 A 1/2017
(Continued)

OTHER PUBLICATIONS

Lee, Won Gu et al; "Nano/Microfluidics for diagnosis of infectious diseases in developing countries." Advanced drug delivery reviews 62.4-5 (2010): 449-457. (Year: 2010).*

(Continued)

*Primary Examiner* — Roy M Punnoose
(74) *Attorney, Agent, or Firm* — Kligler & Associates Patent Attorneys Ltd.

(57) ABSTRACT

A computerized device provides microscopy and electro-chemistry tests, performed in dual channels. The device can be brought to the field, for on-site testing with instant results. The dual channels include an imaging channel and a signal channel.

23 Claims, 13 Drawing Sheets

(51) Int. Cl.
*A61B 5/1468* (2006.01)
*G01N 27/27* (2006.01)
*C12M 1/00* (2006.01)
*B01F 33/30* (2022.01)

(52) U.S. Cl.
CPC .............. *B01F 33/30* (2022.01); *B01L 3/505* (2013.01); *B01L 3/50273* (2013.01); *C12M 27/22* (2013.01); *G01N 27/27* (2013.01); *A61B 2562/0295* (2013.01); *B01L 2300/0822* (2013.01); *B01L 2300/0874* (2013.01); *B01L 2400/0406* (2013.01)

(58) Field of Classification Search
CPC ..... B01L 2400/0406; B01L 2300/0816; B01L 2300/0819; B01L 2300/0867; B01L 2400/0481; B01L 3/5027; B01L 2300/023; B01L 2300/0645; A61B 5/1455; A61B 5/1468; A61B 2562/0295; A61B 5/145; A61B 5/1486; B01F 33/30; C12M 27/22; G01N 27/27; G01N 15/1475; G01N 2015/0073; G01N 2015/008; G01N 21/05; G01N 21/75; G01N 27/26

See application file for complete search history.

(56) References Cited

U.S. PATENT DOCUMENTS

| | | | | |
|---|---|---|---|---|
| 5,732,150 | A * | 3/1998 | Zhou | G01N 1/312 382/164 |
| 6,295,506 | B1 * | 9/2001 | Heinonen | G01N 33/66 600/301 |
| 6,494,830 | B1 * | 12/2002 | Wessel | A61B 5/335 273/459 |
| 6,641,533 | B2 * | 11/2003 | Causey, III | A61B 5/0031 128/903 |
| 6,969,450 | B2 * | 11/2005 | Taniike | G01N 33/4875 204/403.01 |
| 7,738,094 | B2 * | 6/2010 | Goldberg | G01N 21/6456 356/246 |
| 8,145,431 | B2 * | 3/2012 | Kloepfer | G01N 21/78 600/300 |
| 8,804,105 | B2 | 8/2014 | Ayliffe | |
| 8,935,007 | B2 * | 1/2015 | Kloepfer | G01N 33/48785 436/166 |
| 9,377,456 | B1 * | 6/2016 | Herget | G01N 33/54386 |
| 9,488,663 | B2 * | 11/2016 | Di Tullio | G01N 33/54393 |
| 9,658,152 | B2 * | 5/2017 | Zimmerle | G02B 21/0008 |
| 9,658,217 | B2 * | 5/2017 | Chen | H04M 1/185 |
| 9,733,460 | B2 * | 8/2017 | Kang | G02B 21/0064 |
| 10,060,916 | B2 * | 8/2018 | Knopfmacher | G01N 33/53 |
| 10,272,428 | B2 | 4/2019 | McGuinness et al. | |
| 10,436,773 | B2 * | 10/2019 | Depa | A61B 5/00 |
| 10,605,805 | B2 * | 3/2020 | Chou | G01N 1/30 |
| 11,060,994 | B2 * | 7/2021 | Low | G01N 27/3271 |
| 11,067,526 | B2 * | 7/2021 | Low | G01N 21/78 |
| 11,067,564 | B2 * | 7/2021 | Heo | G01N 33/66 |
| 11,400,447 | B2 | 8/2022 | Ezra et al. | |
| 11,534,756 | B2 * | 12/2022 | Turner | B01L 3/502715 |
| 2003/0049849 | A1 * | 3/2003 | Mori | G01N 21/8483 422/66 |
| 2005/0096518 | A1 * | 5/2005 | Chang | A61B 5/0002 600/345 |
| 2005/0158704 | A1 | 7/2005 | Tyvoll et al. | |
| 2006/0222567 | A1 * | 10/2006 | Kloepfer | G01N 21/78 422/68.1 |
| 2008/0058626 | A1 * | 3/2008 | Miyata | A61B 5/150824 600/366 |
| 2008/0058678 | A1 * | 3/2008 | Miyata | A61B 5/1519 600/583 |
| 2010/0331652 | A1 * | 12/2010 | Groll | A61B 5/7445 600/365 |
| 2011/0091357 | A1 | 4/2011 | Blatt et al. | |
| 2011/0184653 | A1 * | 7/2011 | Ray | A61B 5/1486 702/19 |
| 2011/0312644 | A1 * | 12/2011 | Silverbrook | B01L 3/502707 506/39 |
| 2012/0183442 | A1 * | 7/2012 | Kloepfer | G01N 33/66 422/82.05 |
| 2013/0006536 | A1 * | 1/2013 | Kraft | A61B 5/1477 702/19 |
| 2013/0065245 | A1 | 3/2013 | Rutter et al. | |
| 2013/0102018 | A1 * | 4/2013 | Schentag | G01N 21/05 435/25 |
| 2014/0134595 | A1 | 5/2014 | Kurowski et al. | |
| 2015/0301031 | A1 * | 10/2015 | Zin | H04W 4/80 436/164 |
| 2015/0316477 | A1 | 11/2015 | Pollak et al. | |
| 2016/0016171 | A1 * | 1/2016 | Goel | B01L 3/5023 435/7.1 |
| 2016/0019283 | A1 | 1/2016 | Gibson et al. | |
| 2016/0144358 | A1 | 5/2016 | Patel | |
| 2017/0102348 | A1 * | 4/2017 | Neethirajan | G01N 27/3272 |
| 2017/0274378 | A1 * | 9/2017 | Turner | B01L 3/502715 |
| 2017/0341077 | A1 * | 11/2017 | Neethirajan | B01L 3/5027 |
| 2018/0059101 | A1 * | 3/2018 | Mackay | G01N 33/5438 |
| 2018/0100869 | A1 * | 4/2018 | Niemeyer | B01L 3/545 |
| 2018/0292383 | A1 * | 10/2018 | Heo | G01N 33/6893 |
| 2018/0304252 | A1 | 10/2018 | Wei et al. | |
| 2022/0252538 | A1 * | 8/2022 | Reddy | C12N 9/22 |
| 2022/0331797 | A1 | 10/2022 | Ezra et al. | |

FOREIGN PATENT DOCUMENTS

| | | | | |
|---|---|---|---|---|
| CN | 112337515 | A * | 2/2021 | ............. B01F 33/30 |
| EP | 3049800 | A1 | 8/2016 | |
| EP | 3121601 | A1 | 1/2017 | |
| JP | 2014500478 | A | 1/2014 | |
| WO | 9404272 | A1 | 3/1994 | |
| WO | 2004074827 | A1 | 9/2004 | |
| WO | WO-2005088519 | A1 * | 9/2005 | ........... G01N 21/253 |
| WO | 2009067521 | A1 | 5/2009 | |
| WO | 2012047009 | A2 | 4/2012 | |
| WO | 2012061797 | A2 | 5/2012 | |
| WO | 2012122379 | A2 | 9/2012 | |
| WO | 2013158506 | A2 | 10/2013 | |
| WO | 2015173774 | A2 | 11/2015 | |
| WO | 2015195352 | A1 | 12/2015 | |
| WO | 2018009920 | A1 | 1/2018 | |

OTHER PUBLICATIONS

Lee, Won Gu, et al. "Nano/Microfluidics for diagnosis of infectious diseases in developing countries." Advanced drug delivery reviews 62.4-5 (2010): 449-457. Lee, Won Gu, et al Mar. 18, 2010 (Mar. 18, 2010).

Antia, Meher, Thurston Herricks, and Pradipsinh K. Rathod. "Microfluidic Modeling of Cell-Cell Interactions in Malaria Pathogenesis." PLoS pathogens 3.7 (2007): e99 Antia, Meher, Thurston Herricks, and Pradipsinh K. Rathod Dec. 31, 2007 (Dec. 31, 2007).

Ahn, Chong H., et al. "Disposable smart lab on a chip for point-of-care clinical diagnostics." Proceedings of the IEEE 92.1 (2004): 154-173. Ahn, Chong H., et al. Dec. 31, 2004 (Dec. 31, 2004).

Mavandadi, Sam, et al. "Distributed medical image analysis and diagnosis through crowd-sources games: a malaria case study." PLoS one 7.5 (2012): e37245. Mavandadi, Sam, et al. Dec. 31, 2012 (Dec. 31, 2012).

Breslauer, David N., et al. "Mobile phone based clinical microscopy for global health applications." PLoS one 4.7 (2009): e6320. Breslauer, David N., et al. Dec. 31, 2009 (Dec. 31, 2009).

Shelby J. Patrick, et al. "A microfluidic model for single-cell capillary obstruction by Plasmodium falciparum-infected erythrocytes." Proceedings of the National Academy of Sciences 100.25 (2003): 14618-14622. Shelby J. Patrick, et al. Dec. 31, 2003 (Dec. 31, 2003).

Horning, Matthew P. et al. "A paper microfluidic cartridge for automated staining of malaria parasites with an optically transparent

(56) References Cited

OTHER PUBLICATIONS microscopy window." Lab on a chip 14.12 (2014): Dec. 31, 2014 (Dec. 31, 2014).
Berg, Brandon, et al. "Cellphone-based hand-held microplate reader for point-of-care testing of enzyme-linked immunosorbent assays." ACS nano 9.8 (2015): 7857-7866. Berg, Brandon, et al. Dec. 31, 2015 (Dec. 31, 2015).
Gascoyne, Peter, Jutamaad Satayavivad, and Mathuros Ruchirawat. "Microfluidic approaches to malaria detection." Acta tropica 89.3 (2004): 357-369. Gascoyne, Peter, Jutamaad Satayavivad, and Mathuros Ruchirawat. Dec. 31, 2004 (Dec. 31, 2004).
<http://www.path.org/news/press-room/784/> Kate Davidson Nov. 10, 2016 (Nov. 10, 2016).
Wikipedia Page entitled "MYCIN" (3 Sheets) dated Sep. 27, 2021.
Korean Application # 10-2019-7025536 Office Action dated Aug. 22, 2022.
International Application PCT/IL2018/050132 Search Report dated May 10, 2018.
International Application PCT/IB2022/060511 Search Report dated Mar. 13, 2023.
IL Application # 268548 Office Action dated Jun. 26, 2022.
IN Application # 201917034629 Office Action dated Jul. 1, 2021.
European Application # 18748298.9 Office Action dated Jul. 16, 2020.
European Application # 18748298.9 Search Report dated Nov. 27, 2019.
Australian Application # 2018215821 Office Action dated Feb. 18, 2022.
Japanese Application # 2019-539851 Office Action dated Aug. 19, 2021.
CN Application # 201880010387.5 Office Action dated Jan. 11, 2022.
CN Application # 201880010387.5 Office Action dated Aug. 11, 2021.
CN Application # 201880010387.5 Office Action dated Feb. 26, 2021.
Peihua et al., "Application of Microcomputer in Medical Inspection", Shanghai Science and Technology Press, p. 245, Nov. 30, 1993.
U.S. Appl. No. 17/851,276 Office Action dated Sep. 20, 2023.

* cited by examiner

PORTABLE DIGITAL DIAGNOSTIC DEVICE

CROSS REFERENCES TO RELATED APPLICATIONS

This application is related to and claims priority from commonly owned U.S. Provisional Patent Application Ser. No. 62/454,933, entitled: Portable Digital Diagnostic Device, filed on Feb. 6, 2017, the disclosure of which is incorporated by reference in its entirety herein.

TECHNICAL FIELD

The present invention is directed to portable apparatus for onsite disease diagnosis.

BACKGROUND

Numerous clinical tests require a blood sample to be taken in order to provide a diagnosis. Presently, the patient must give a blood sample, either on or off site, and then wait for test results, as the blood sample must be taken to a laboratory for analysis, typically by microscopy, performed by trained personnel. Even getting the blood sample must be done by trained personnel, using syringes, butterfly needles, blood tubes and other blood collection devices. The blood collection devices must be stored properly and maintained in a sanitary manner, so as not to become contaminated and thus, cannot be used. Also, once the blood sample reaches the microscopist, it must be properly "smeared", in order to be usable for microscopy or other analysis.

Microscopy is the "gold standard" for laboratory analysis. In more than 50% of the world, clinics with microscopic equipment are rare, as well as trained microscopists to prepare operate the microscopy equipment and provide a diagnosis of the blood or tissue sample. Moreover, obtaining a test result from microscopy takes time, and is certainly not instantaneous, even if the microscopy lag and microscopist are on site, at a medical clinic, hospital, or the like. Also, in many parts of the world, trained microscopists and laboratories with suitable microscopic equipment for the microscopist are limited, and may be far away from various populations, such as rural populations, adding additional difficulty to getting a blood test with a result determined by microscopy.

There are also problems associated with transporting a blood sample to a microscopy laboratory, due to possible improper handling of the sample, as well as possible spoliation of the sample, due to weather and time in transit, from the patient to the laboratory. Such blood tests are also expensive to many people in the world, eliminating many people from getting such tests. Moreover, as the result is not instant, and typically off site, patients may not be able to be charted for statistical studies, and infected patients who require immediate treatment may not be able to be located quickly.

Rapid Diagnostic Tests (RDTs) provide instant results. However, there are not RDTs for many diseases and the detection of disease is without significant sensitivity which is needed for early detection and typically has poor specificity. These RDT devices must be properly stored and handles, so as to maintain accuracy and reliability. Also, there are many manufactures of RDTs and quality of the RDTs varies greatly between manufacturers.

As diseases spread rapidly, it is important to diagnose them quickly and in the early stages. This ensures that patients can be treated quickly, so as to maintain their health, as well as prevent the disease from spreading. In many locations all over the world, this is simply not possible, due to the lack of laboratory facilities, coupled with the lack of trained experts who can properly identify diseases.

Also, for some diseases, such as malaria, additional tests are needed, such as a Glucose-6-phosphate Dehydrogenase (G6PD) deficiency test—in order to decide on the safest and proper treatment (based on WHO guidelines for malaria elimination and eradication). This test, in addition to the malaria diagnostics, is typically not available and not accessible in many rural and remote locations areas of the world.

SUMMARY

The present invention provides a computerized device which brings microscopy and electrochemistry tests to the field, for on-site testing with instant results, for example, in real time with minimally trained operator that can be a community-health-work and not only physician The computerized device is a single hand held device, which can be brought to remote areas, giving millions of people access to healthcare that they did not have previously. Since instant results are obtained, the unnecessary use of drugs, such as un-necessary antibiotic and/or antimalarial is eliminated, as diseases and conditions are provided with certainty, on the spot. Additionally, since disease and conditions are detected instantly, treatment protocols can begin immediately, eliminating the spread of infectious and deadly diseases and conditions.

The computerized device is a dual channel device, one channel for imaging or microscopy, and one channel for electrochemistry (signals). Based on results from these two channels, a diagnosis can be made that is more accurate and effective than is presently possible in the field. This allows for rapid and safe treatment and follow-up of disease, inhibiting its spreading, as well as allowing for real-time mapping patients, in order to track movement of diseases in real-time and obtain other data for immediate and effective intervention of health authorities, studies, and the like. The device is, for example, a lab-on-hand computerized platform, which is programmable for various medical diagnostic applications based on the same RevDx hardware platform The disclosed device allows for receiving a blood sample, that can be taken by the user or medical personnel with little or any training, with a finger prick, and does not need trained medical personnel. The disclosed device, is designed to be coupled to a mobile device or mobile computer, such as a smart phone, with the device designed for analyzing the blood sample, and provide an instant diagnosis on site and in real time. As the device performs its analysis by techniques such as machine learning, and other network connectivity, such as telemedicine, where the image of the blood sample, is transmitted over a network, such as the internet, to trained medical personnel, in remote locations.

By obtaining this sensitive and accurate diagnosis instantly, the patient can be treated much sooner that would be done conventionally. This preserves the health of the patient, and where the disease is contagious, prevents that disease from spreading.

The present invention uses disposable sample preparation kit based on microfluidic technologies and or biosensor/electrochemistry strips, with corresponding reading and analysis systems to diagnose different or dual aspects of diseases, typically on site. For example, with Malaria, the microfluidic chips, accompanied by their reading and analysis, are able to detect the malaria parasite type with a high sensitivity and specificity, allowing for detection of malaria in early stages, where parasite density is low (when compared to advanced stages of Malaria). The biosensor strip and reader channel is used to detect G6PD deficiency. This is essential to ensure that treatment with the drug primaquine used for the malaria parasite *Plasmodium vivax* is administered safely. In addition, primaquine is used to prevent transmission of other malaria parasites types. The biosensor reader channel will also be used for glucose level monitoring. As malaria can cause hypoglycemia (dangerously low level of glucose), this will aid in deciding which patients need admission to a hospital.

Moreover, as the microfluidic chip and biosensor strip are both disposable and receive a blood sample at the time of testing, the process is sanitary, as disease does not pass between patients being tested, accurate, as there is no chance of blood spoliation, and many patients can be tested in a small amount of time by minimally trained or untrained medical personnel. Additionally, the micro fluidic chips and biosensor strips require small amounts of blood, usable as blood smears. The blood is obtained, for example, by a finger prick, which can be performed by the user or someone without medical training or with minimal medical training.

Also, the process is inexpensive, as the microfluidic chips and biosensor strips are inexpensive, with the device used being a one-time purchase, capable of multiple uses.

Embodiments of the present invention are directed to a device for analyzing disease conditions. The device comprises: an imaging channel configured for providing a viewable sample; and, a signal channel including a signal analyzer for analyzing received signals based on electrochemical responses emitted from an electrode having reacted to a sample, to determine the existence of the disease condition.

Optionally, the device additionally comprises: an analytics module configured for scanning an image of the viewable sample, and determining the existence of the disease condition from the scanned image.

Optionally, the analytics module is configured for determining, from the scanned image, the existence of a disease condition selected from the group consisting of: G6PD deficiency output, blood glucose levels, malaria parasites including, *P. falciparum, P. vivax, P. malaria. P. ovale, P. knowlesi* and the disease stage, complete blood cell counts, multi-parasites including relapsing fever and Filarias, Tuberculosis, Pap smear analysis, urine tests and/or analysis and veterinary diseases Optionally, the device additionally comprises: an optomechanical system for magnifying and scanning the sample, the optomechanical system in communication with the analytics module.

Optionally, the device additionally comprises: a processor programmed to determine a treatment for the disease condition, the processor in communication with the analytics module.

Optionally, the device additionally comprises: a processor programmed to determine a treatment for the disease condition, the processor in communication with the analytics module and the signal analyzer.

Optionally, the imaging channel and the signal channel are configured to output the determination of the existence of the disease condition in real time.

Optionally, the device includes a display in communication with the imaging channel and the signal channel.

Optionally, the display includes one or more of: 1) a screen display, and, 2) a display output configured for communicating with an image sensor of an external computer device for displaying graphics on the display screen of the external computer device.

Optionally, the imaging channel includes a first end for receiving the sample, and an oppositely disposed second end associated with the display.

Optionally, the device additionally comprises: an analog to digital signal converter (ADC) in communication with the signal analyzer; and, a signal reader for reading the electrochemical signals (e.g., analog signals) emitted from the electrode having reacted to the sample, the signal reader in communication with the ADC.

Optionally, the signal analyzer is configured for analyzing signals determine disease conditions selected from the group consisting of: G6PD output, blood glucose levels, malaria parasites including: *P. falciparum, P. vivax, P. malaria. P. ovale,* and the disease stage, complete blood cell counts, multi-parasites including: relapsing fever and Filarias, Tuberculosis, Pap smear analysis, and veterinary diseases.

Optionally, the device additionally comprises: a processor programmed to transmit data to the display which causes presentation of a User Interface (UI) graphic display of the presence the disease condition.

Optionally, the device additionally comprises: a location module in communication with at least one of the imaging channel or the signal channel, the location module configured for displaying real-time location indications based on Global Positioning System (GPS) mapping of the detection of the disease condition.

Optionally, the device additionally comprises: a first port for receiving a microfluidic chip holding the sample for being rendered viewable in the imaging channel; and, a second port for receiving an electrode holding the sample in the signal channel.

Optionally, the device additionally comprises: a microfluidic chip for sample preparation for receipt in the first port.

Optionally, the device additionally comprises: a biosensor strip including an electrode for producing an electrochemical response when contacted by a sample, for receipt in the second port.

Optionally, the sample includes portions of the same sample and the sample includes at least one of blood, urine, and tissue.

Optionally, the microfluidic chip is configured for mixing the sample, with one or more of staining agents, imaging enhancers, and dilatants.

Embodiments of the invention are directed to a method for analyzing, for example, automatically analyzing, disease conditions. The method comprises: providing a sample to an imaging channel of a device including a display for viewing on the display; and, providing a sample to a signal channel of the device, the device including a signal analyzer, and the signal analyzer analyzing received signals based on electrochemical responses emitted from an electrode having reacted to the sample, to determine the existence of the disease condition.

Optionally, the method is such that information as to the disease condition detected by signal analyzer is displayable on the display.

Optionally, the method is such that the sample provided to the imaging channel and the sample provided to the signal channel include portions of the same sample and the sample includes at least one of blood, urine, and tissue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings, where like reference numerals or characters represent corresponding or like elements. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawing figures where like reference numerals or characters refer to corresponding or like components. The drawing figures are as follows.

DETAILED DESCRIPTION OF THE DRAWINGS

Figure 1:
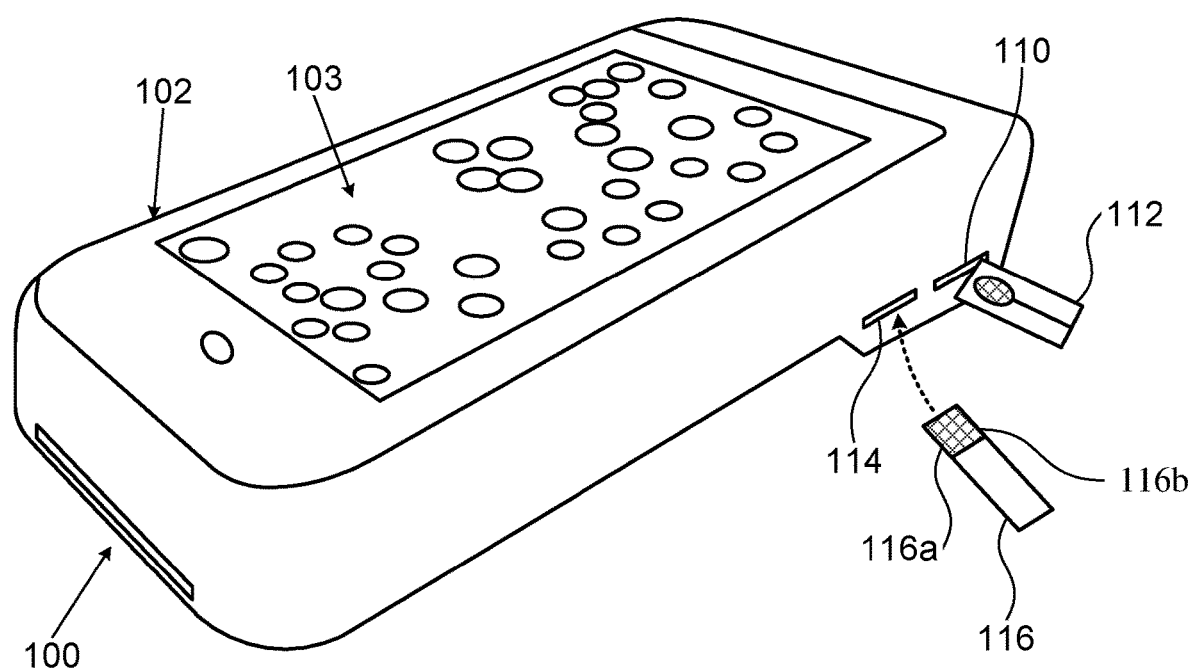
FIG. 1 is a diagram showing an exemplary environment in which embodiments of the invention are performed.

FIG. 1 shows an example embodiment of the invention, where an electronic device 100, in the form of a base (the electronic device 100 also known as a base, with these terms being used interchangeably herein), receives a mobile computing device, for example, a smart phone 102, including a display screen 103, in a mechanical engagement, so as to be directly linked to the optics and in electronic and/or data communication to each other. The base 100 and smart phone 102 may also be linked to each other through communications networks, such as a wide area or public network such as the Internet. There may also be linking via near field communications and other electronic communication formats and direct links through an Input/Output (I/O) port of a communications module 254 (FIG. 2).

The base 100 includes one port 110 for receiving a disposable sample preparation chip/cassette based on microfluidic technologies 112, on which is, for example, a blood sample, for analysis, and another port 114 for receiving a biosensor strip 116, which receives a blood sample, at an operative end 116a, for example, on an electrode 116b. The ports 110, 114 are associated with channels. Port 110 serves as the inlet for a microscopy or imaging or microscopic channel (the terms "imaging channel", "microscopic channel" and "optic/optical channel" used interchangeably herein), for example, with malaria, identifying the specific parasite (type of malaria) and the stage of malaria and also for Complete Blood Count (CBC) applications. The other port 114 serves as a signal channel or electrochemical channel ("signal channel" and "electrochemical channel" used interchangeably herein), for analyzing electrochemical signals from the blood sample on the electrode 116b of the biosensor strip 116, and for example, for malaria infected patients, determining whether there is a Glucose-6-Phosphate Dehydrogenase (G6PD) deficiency to decide on the appropriate and precise medication.

Figure 2:
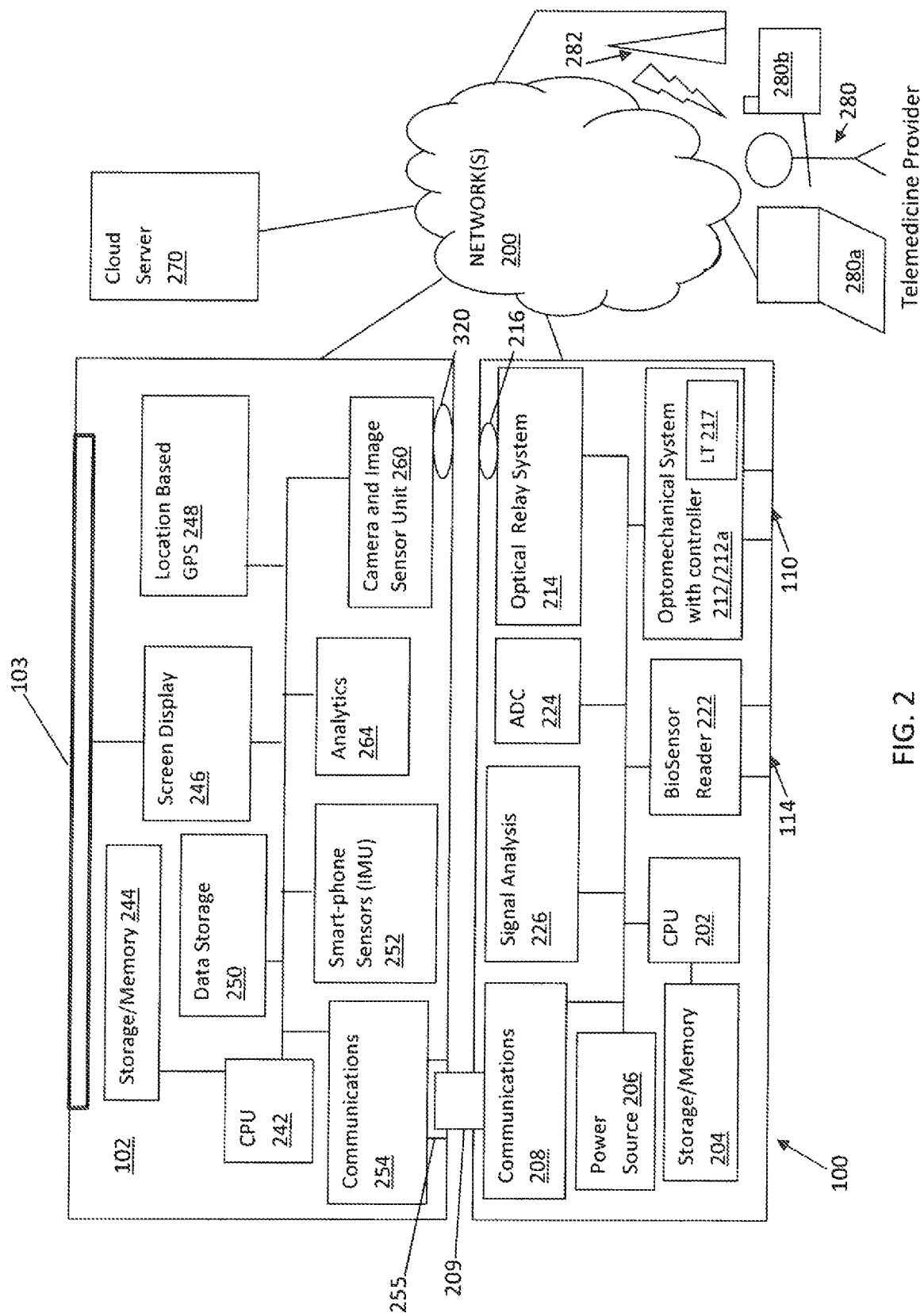
FIG. 2 is a block diagram of the base and computer device as used in combination, also showing how these devices are linked to networks.

FIG. 2 shows a block diagram of the base 100 and the smart phone 102. The base 100 and smart phone 102 are shown directly connected to each other, and are linked to one or more networks 200, such as local area networks (LANs), and wide area networks (WANs), including public networks, such as the Internet, cellular networks and other communications networks.

Both channels, the imaging channel, from port 110, and the signal channel, from port 114, use a common central processing unit (CPU) 202, with linked storage/memory 204, a power source 206 for the base and a communications module 208, from which a male type USB (universal serial bus) connector 209 or other similar connector, extends.

The central processing unit (CPU) 202, is formed of one or more processors, in electronic and data communication with storage/memory 204, which stores machine executable instructions for execution by the CPU 202, to perform the processes of the dual channels. The power source 206 is a battery or plug-in power source. The communications module 208 provides network (e.g., Internet) connectivity and communication to and from the base 100, in addition to providing the direct connection, for electronic and data communication between the base 100 and the smart phone 102.

The imaging channel includes the port 110, which receives a microfluidic chip 112 (FIG. 1). The microfluidic chip 112 is made viewable by optics 308 (FIG. 3), including an optomechanical system 212, and an optical relay system 214, and ends in an optical module lens 216, through which an image is transmitted. The optics 308, for example, the opotomechanical system 212, magnifies the sample and enhances the visual presentation, including images, to being able to achieve high-resolution of microns, thereof.

The microfluidic chip 112 operates based on capillary action, to transport the received blood, and stain it, in order to be properly viewed. An optomechanical system 212 (with a controller 212a) provides for scanning the microfluidic chip 112 (the scanning provided by movement of a stand/drawer 302 on a scanning mechanism 304 (FIG. 3) by the controller 212a) for microscopic viewing, by an optical relay system 214, which terminates in an optical module lens 216. There is also a light (LT) 217 as part of the optomechanical system 212, which may be controlled manually (via a switch, button or the like (not shown)) or the controller 212a. The optomechanical system 212 and optical relay system 214 are in electronic and/or data communication either directly or indirectly with the CPU 202, storage/memory 204, power source 206, and the communications module 208.

FIGS. 6A-6D show various microfluidic chips 112a-112d, respectively.

Figure 6A:
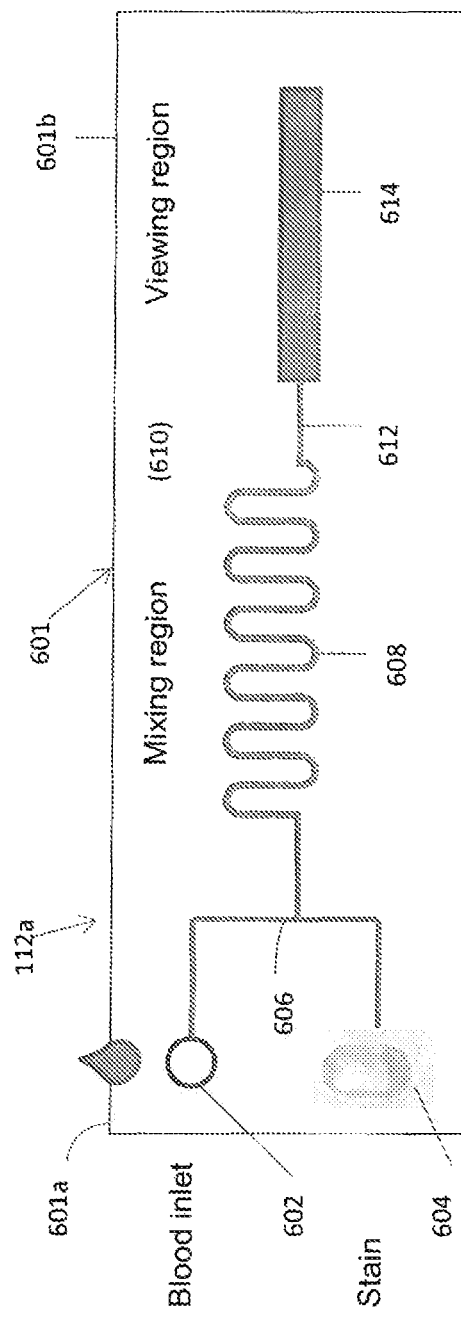
FIGS. 6A-6D are illustrations of microfluidic apparatus for the disclosed devices.

The microfluidic chip 112a shown in FIG. 6A includes a substrate 601, of glass or polymer or both or other material with/without hydrophilic coating, suitable for supporting blood and other fluids such as urine and other components, e.g., stain, for microscopy. On the substrate 601 is a blood inlet 602, and a stain, encased in a blister (packet) 604, at one end of the substrate 601a. When use is desired, pressure on the blister 604 ruptures the blister 604 from the tunnel side and press the stain through the microfluidic tunnel 606. The blood and/or a diluted blood and stain travel via a microfluidic channel 606 to a serpentine shaped microfluidic channel 608 which serves as a mixing region 610 for the blood and stain. The combines blood and stain, both still moving, travel through another microfluidic channel 612 to a viewing chamber 614, at an opposite end 601b of the substrate. The viewing region 614 is configures on the substrate 601 to align with the optics 308 of the optomechanical system 212 of the apparatus 100, 500.

Figure 6B:
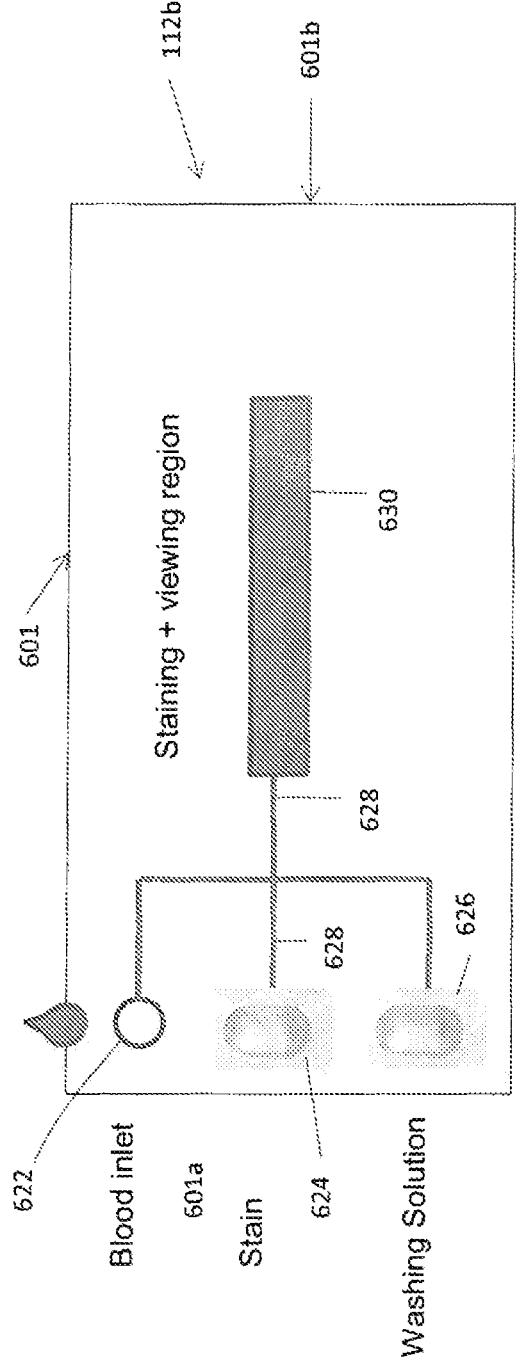

The microfluidic chip 112b shown in FIG. 6B includes a substrate 601, for supporting blood and other components, e.g., stain, washing solution, for microscopy. On the substrate 601 is a blood inlet 622, a stain, encased in a blister (packet) 624, and a washing solution, encased in a blister (packet) 626, at one end of the substrate 601a. When use is desired, blood from the blood inlet 622 flows through the microfluidic channel 628, leaving blood cells adhered to the walls of the microfluidic channel 628. Pressure on the blister 624 ruptures the blister 624, causing the stain to flow through the microfluidic channel 628 over the adhered blood cells, such that stain and cells reach the staining and viewing region 630 on the substrate 601. The staining and viewing region 630 is configured on the substrate 601 to align with the optics 308 of the optomechanical system 212 of the apparatus 100, 500. Next, pressure on the blister 626 ruptures the blister 626, causing the washing solution to flow through the microfluidic channel 628 removing any residual stain and dilute the blood-stain mixture.

Figure 6C:
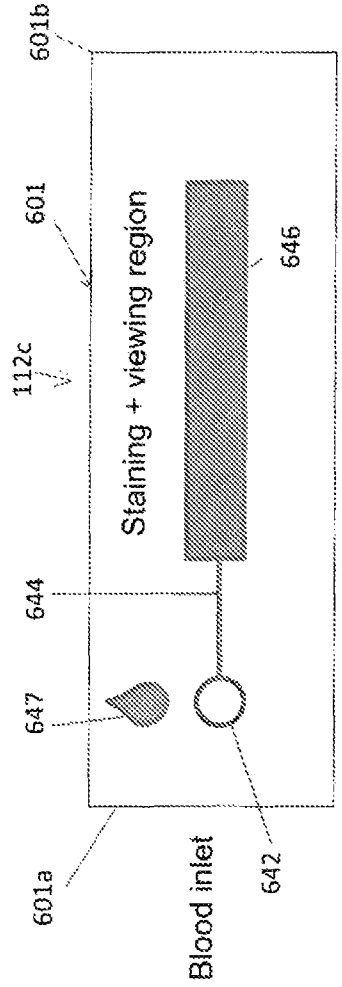

The microfluidic chip 112c shown in FIG. 6C includes a substrate 601 for supporting blood and other components, e.g., stain, for microscopy. On the substrate 601 is a blood inlet 642 (at one end 601a of the substrate 601), which is at the end of a microfluidic channel 644, which ends in a staining and viewing chamber 646 (at the other end 601b of the substrate 601). The staining and viewing chamber 646 is configured on the substrate 601 to align with the optics 308 of the optomechanical system 212 of the apparatus 100, 500. Stain, in a dry state, is contained in the walls of the microfluidic channel 644, such that as blood or a diluted blood 647 flows through the microfluidic channel 644 to the staining and viewing region, the blood 647 picks up stain. This microfluidic chip 112 is typically used for viewing single red blood cells. Here, the microfluidic channel is shallow, approximately 10 micrometers in diameter, since the blood is not being diluted.

Figure 6D:
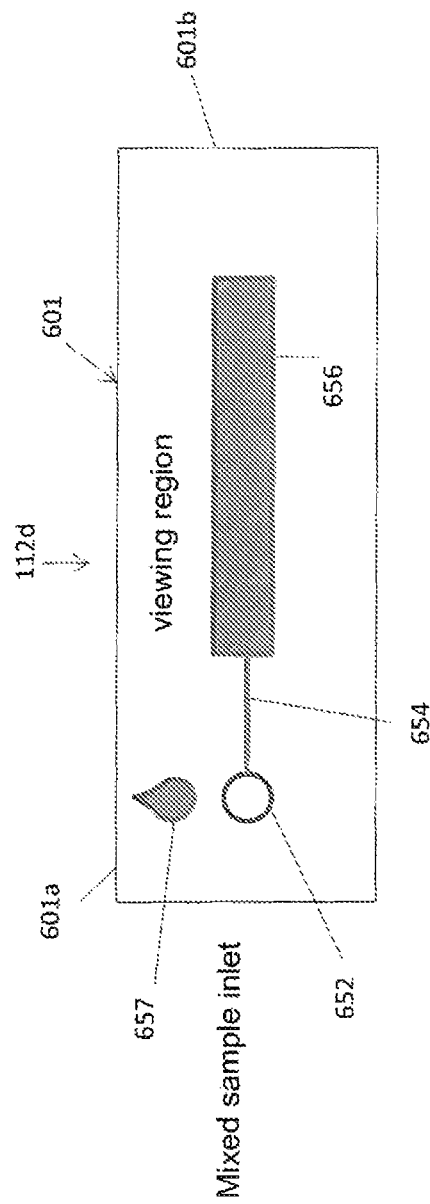

The microfluidic chip 112d shown in FIG. 6D includes a substrate 601, for supporting blood and other components. The substrate 601, at one end 601a supports a sample inlet 652, which joins a microfluidic channel 654, which, in turn, joins and terminates at a viewing chamber 656, at the other end 601b of the substrate 601. A blood sample, diluted or non-diluted mixed with a stain 657 is placed into the sample inlet 652, where the stained sample flows to the viewing chamber 656. The viewing chamber 656 is configured on the substrate 601 to align with the optics 308 of the optomechanical system 212 of the apparatus 100, 500.

The signal channel originates at the port 114, and includes a bio-sensor strip reader 222, which reads the electrical response (generated electrical current from the electrochemical reaction between the sample and the electrode 116b, output from the electrode 116b/biosensor strip 116 as an analog signal) from the disposable biosensor electrode 116b (e.g., at the operative end 116a of the biosensor strip 116), and amplifies the analog signal of the electrical response, the analog signal indicative of the electrochemical reaction, for a disease, condition, measurement, or the like. There is an analog to digital converter (ADC) 224 which converts the analog signals from the reader 222 to digital signals, a signal analysis software module 226, which analyzes the digital signals to decide whether or not there is a G6PD deficiency in this sample, and which communicates with the communications module 208, to send the signals to the smart phone 102, for additional analysis.

Alternately, the signal channel can be used for blood glucose level detection. The biosensor strip reader 222 is additionally configured to amplify the analog signal(s), generated from the electrical response, from the disposable biosensor electrode (e.g., biosensor strip 116). The analog signals correspond to blood glucose levels. The analog to digital converter (ADC) 224 converts the analog signals from the reader 222 to digital signals, and a signal analysis module 226, analyzes the digital signals received from the ADC 224, to determine the blood glucose level in the blood sample. This blood glucose level is output in accordance with standard measurements for blood glucose, to the communications module 208, to send the signals to the smart phone 102, for additional analysis, and for presentation on the display screen (of the smart phone 102 or stand-alone device 500, 500' (FIGS. 5A and 5B)).

Alternately, biosensor strips 116 may include multiple biosensor electrodes 116b, including electrodes for producing electrical responses, convertible into signals readable for detecting G6PD deficiency and blood glucose levels contemporaneously, and for example, simultaneously.

In other alternatives, the signal channel is usable for other conditions, such as other diseases, pathogens or biomarkers. The biosensor strip reader 222 is additionally configured to amplify or otherwise modify the analog signals produces by the electrical response (electrochemical response) from the electrode on the disposable biosensor strip. The electrode on the biosensor strip is configured to create an electrochemical reaction when contacted by a sample with the condition, the electrochemical reaction creating a current and corresponding analog signal for the condition (the biosensor strip reader is configured to recognize the electrochemical signature (or electrochemical response) of these conditions, and amplify the resultant analog signal caused by the electrochemical response). The analog to digital converter (ADC) 224 converts the analog signals from the reader 222 to digital signals, and a signal analysis module 226 (programmed to determine the condition, e.g., presence of absence thereof), analyzes the digital signals received from the ADC 224, to determine the condition. This condition determination is output, to the communications module 208, to send the signals of this determination to the smart phone 102, for presentation on the display screen (of the smart phone 102 or stand-alone device 500, 500' (FIGS. 5A and 5B)).

The device, for example, the smart phone 102 includes portions of both the microscopy channel and the signal channel. The smart phone 102 includes a common central processing unit (CPU) 242, with linked storage/memory 244, a screen display module 246, which includes logic for controlling the screen display 103 of the smart phone 102, a Global Positioning System (GPS) module 248, data storage 250, such as RAM (Random Access Memory), sensor 252, such as gyrometer, temperature, magnetometer and accelerometer, forming the internal measurement unit (IMU), and a communications module 254, including a female type USB (universal serial bus) connector 255 or other similar connector, for receiving the male connector 209 in electronic and/or data communication. The GPS or location module 248 functions to provide the display of a real-time location indications, based on the incorporated GPS unit (of the smart phone 102 or as part of the standalone device GPS or location module 548) by mapping of the disease to be used for real-time mapping and epidemiologic control and learning of the diseases such as malaria.

There is also a camera/image sensor unit 260, for converting the camera image to signals for display on the screen display 103 (via the screen display module 246), an analytics module 264, for image analysis to detect, for example, the type of malaria parasite (e.g. Plasmodium. falciparum, P. vivax, P. malaria. P. ovale, P. Knowlesi and the disease stage) and perform tagging of the data associated with the particular blood sample. Alternately, the analytics module 264 can be programmed to analyze and detect other diseases and conditions including, complete blood counts, multi-parasite (e.g. relapsing fever, Filarias), Tuberculosis sputum microscopy, Urine analysis, Pap smear analysis, and the like, and also veterinary diseases and conditions.

Both the base 100 and smart phone 102 link, via the network(s) 200 to a cloud server 270, where each frame sample of malaria parasite, is transmitted to (either directly or from the data storage 250), in order to update the machine learning of the analytics module 264, cumulatively. With each new image frame sample, the cloud server 270 sends the updated machine learning to the analytics module 264, in order that it can better detect the malaria parasites. This is done on-line or off-line whenever a connection is available, automatically or by-request. The cloud server 270 also, for example, stores each test record taken, the time, location, diagnosis (both of the parasite and G6PD) patient information and symptoms and more by both the machine 102 and optionally, the diagnosis from a telemedicine provider 280, screen display, and other information, and can map the malaria cases in real-time. All data storage and data transmissions over the networks(s) 200 between any of the base 100, smart phone 102, cloud server 270, telemedicine provider computers 280a, 280b are in accordance with HIPAA (Health Insurance Portability and Accountability Act).

The base 100 and smart phone 102 also link, via the network(s) 200 to a telemedicine provider 280, via a computer 280a or a smart phone 280b (via a cellular tower 282), for example. The telemedicine provider 280 can provide a diagnosis, that is sent either to the cloud server 270 or back to the analytics module 246 of the smart phone 102.

Figure 3:
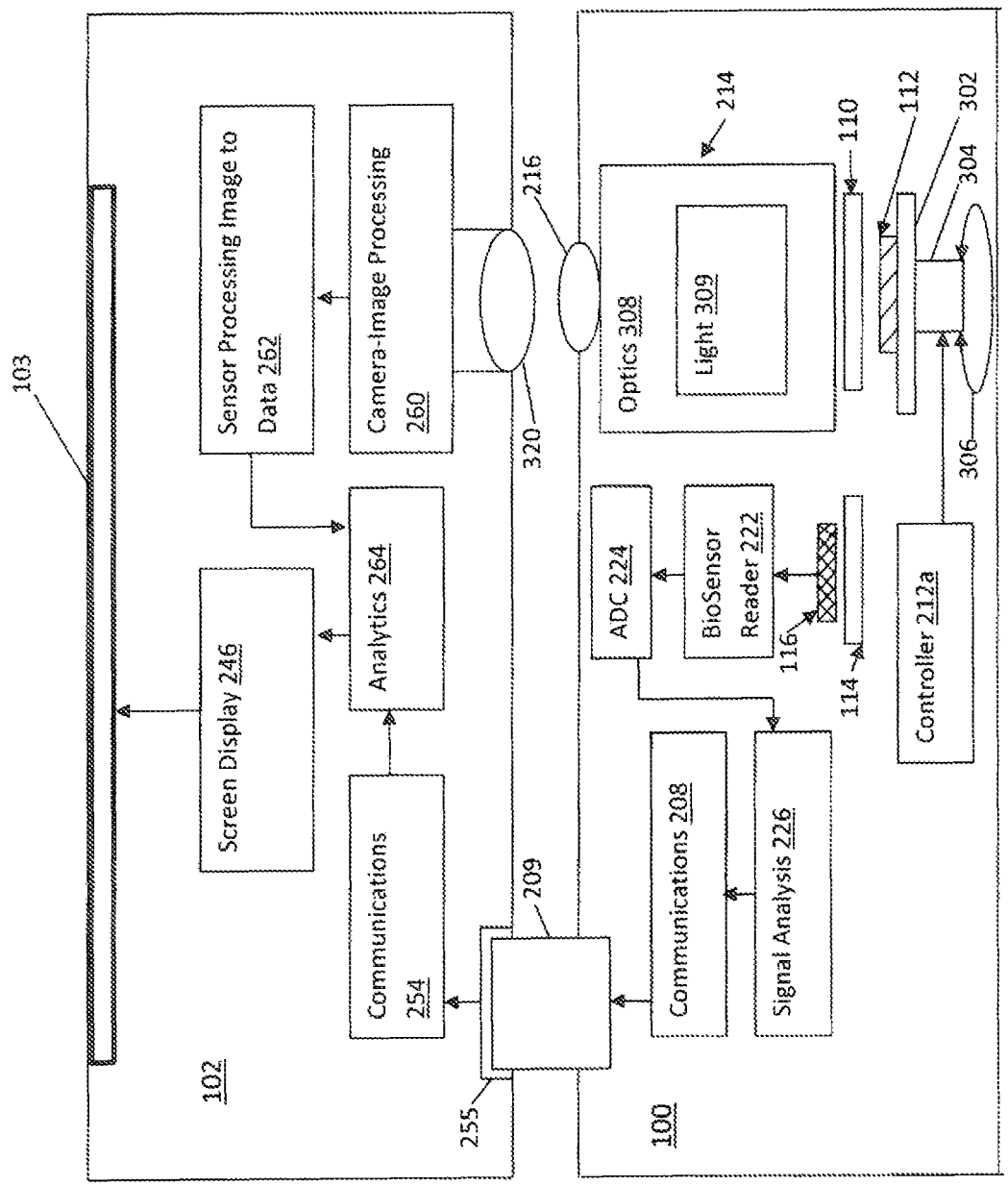
FIG. 3 is a schematic diagram of the base and computer device as used in combination.

FIG. 3 shows schematics of the imaging channel and the signal channel. These channels are in portions in both the base 100 and the smart phone 102.

The microscopy channel originates at the port 110, which receives the microfluidic chip 112. This chip 112 uses capillary action to distribute the blood sample and properly stain it and separate the blood cells. The optomechanical system 212 includes a stand or a drawer 302 which holds the microfluidic chip 112. The stand/drawer 302 is on a scanning mechanism 304 controlled by the controller 212a, which allows the chip 112 to be manipulated to various positions (represented by the double headed oval arrow 306) as per for viewing by the optics 308 of the optical relay system 214, which terminates in a lens 216 or the like. The screening mechanism (formed by the stand/drawer 302 and scanning mechanism 304) is, for example, based on the drawer 302 movement or the optically screened, based on the optical design, e.g., using mirror or prisms (which are part of the optical relay system 214).

The image from the optics 308 (including a light 309 (similar to the light 217 detailed above)) of the optical relay system 214 is transmitted to the lens 320 of the camera 260 of the smart phone 102 or to the stand alone image sensor in case of a stand-alone device. The image from the camera 260 is converted to signals by the image sensor unit 262, with the output signals being input into the analytics module 264. The output signals also go from the analytics module 264 to the screen display module 246, so that the blood sample is displayed on the display screen 103.

The analytics module 264, trained by processes including image analysis, machine learning and artificial intelligence (AI), to determine the disease or condition and provide a diagnosis and/or treatment protocol for the detected disease or condition. Also, the CPU 202 serves to provide a diagnosis and/or treatment protocol for the detected disease or condition. This detection and/or diagnosis of the disease and/or condition is, for example, based on morphological "biomarker" analysis of the parasites in their different stages and type. The algorithm (executed by the controller 212a) includes image processing capabilities (in software and/or hardware), segmentation capabilities (in software and/or hardware), filters and specific morphological comparison to known and collected data from the RevDx system The resultant diagnosis data is stored in the data storage 250 and/or in the cloud server 270. For example, it is also be transmitted to the telemedicine provider 280 for confirmation.

The signal channel originates at the port 114. A blood sample on a biosensor strip 116 is placed into the port 114 and the electrical response (electrochemical response), derived from the electrochemical reaction, which produces correlated analog signals. The analog signals are read by the biosensor reader 222, which amplifies the correlated analog signal. The biosensor reader 222 amplifies and, in some cases filters, the analog signal, which is converted to a digital signal by the analog to digital converter (ADC) 224. The ADC 224 output of the digital signal(s) is input into the signal analysis module 226, which analyzes the digital signal input, for G6PD deficiency, for example. A data corresponding to the presence of G6PD from the sample is sent by the signal analysis module 226 to the communications module 208 and then to the communications module 254 of the smart phone 112. Now in the smart phone 112, the data is sent from the communications module 254 to the analytics module 264, where it is analyzed for recommended medicine based on known treatment procedures. The analytics module 264 signals the screen display module 246 to display on the display screen 103, a graphic listing whether there is a G6PD deficiency and the type of malaria parasite, what species, its density, stage and other factors.

Figure 7:
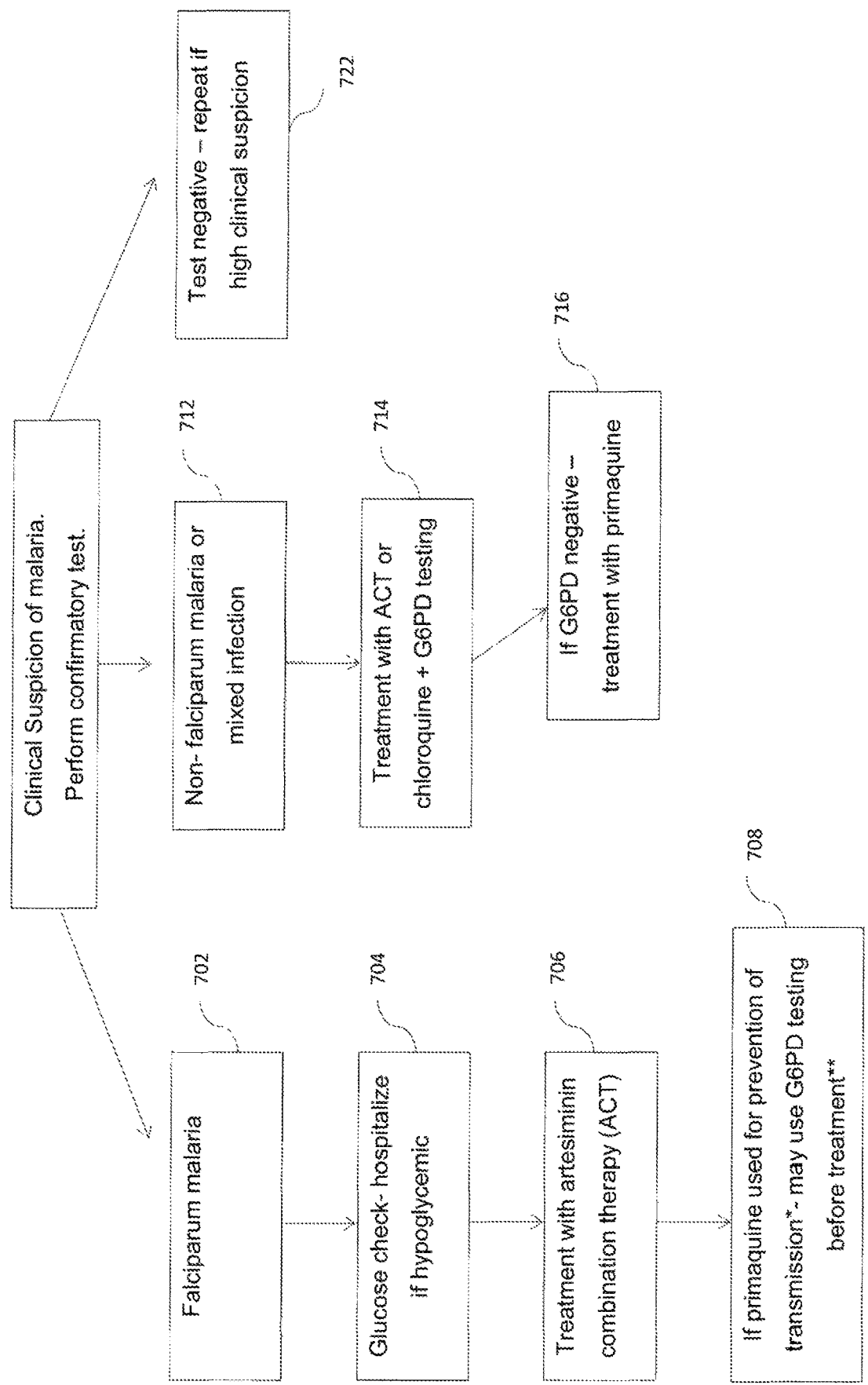
FIG. 7 is a flow diagram of a process performed by the disclosed devices for determining malaria and if, detected, issuing a treatment protocol; and, FIGS. 8A-8D are screen diagrams of the device of FIGS. 5B and 5C while the device is in operation.

Alternately, should the signal channel be constructed to provide blood glucose readings, as detailed above, such blood glucose readings may be obtained with the G6PD output, or separately therefrom, depending on the electrode (s) 116b on the biosensor strip 116. For example, the G6PD result, coupled with a glucose level is analyzed by the CPU 202 to determine a treatment protocol, for example, as shown in FIG. 7. The treatment protocols, as well as the presence of a disease or condition is displayed on display screens, smart phone 103, or stand-alone device 500, 500' as a user interface (UI), as directed by the CPU 202 in the disclosed devices 100, 500, 500'.

The ultimate decision as to the malaria treatment protocol, should malaria be detected, is based on an analysis from both the microscopy channel and the signal channel. This analysis is performed, automatically by the algorithm (run for example by the CPU 202) on-site in few minutes or in case of uncertainty, the data can be sent on the internet and analyzed, remotely by a telemedicine provider 280, via networks 200.

Similarly, should the signal channel be configured to provide other readings of diseases and conditions from the blood, including G6PD output, blood glucose, or from urine tests. One of more of the aforementioned are analyzed together, as programmed into the CPU 202, to determine a treatment protocol.

Figure 4A:
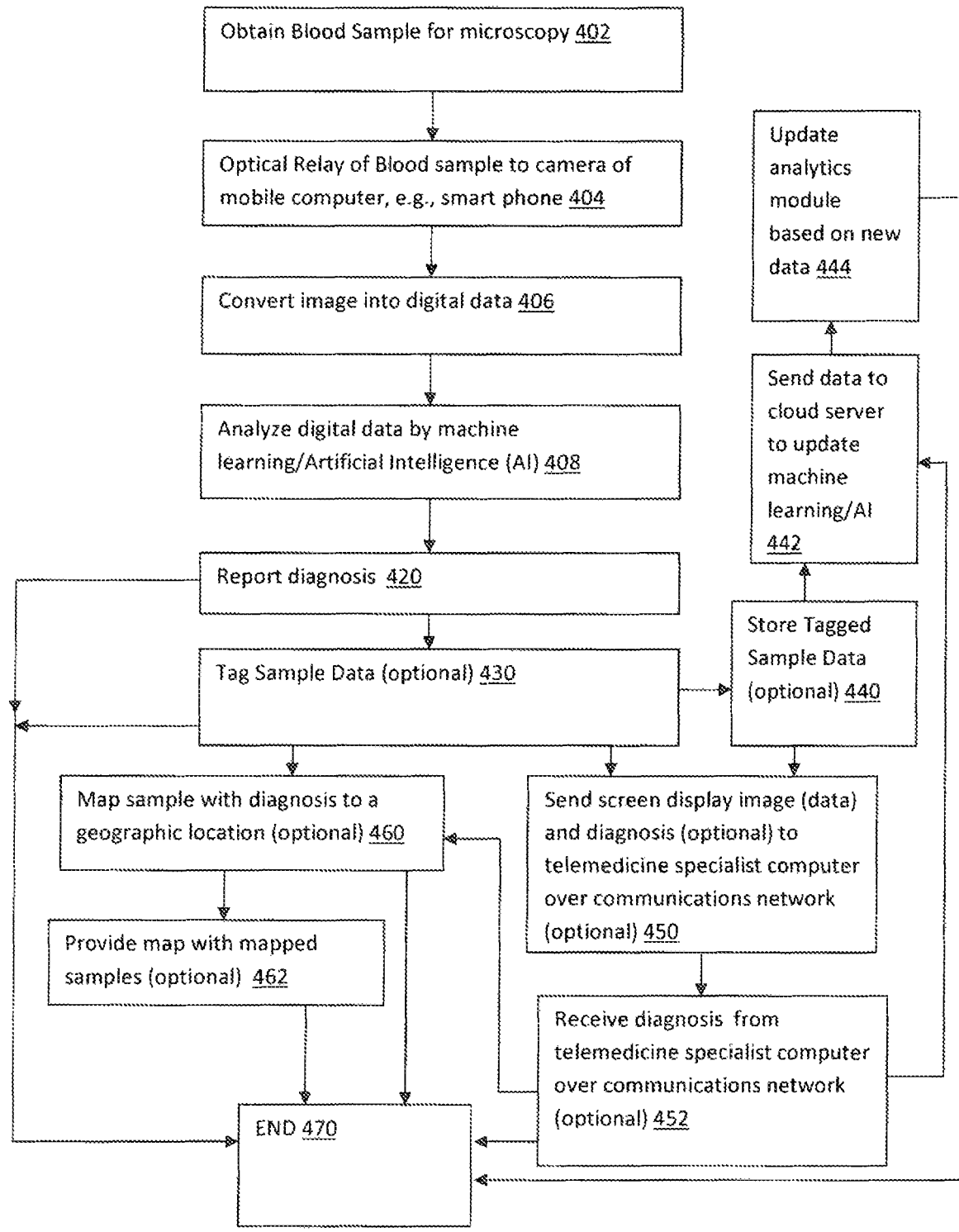
FIG. 4A is a flow diagram for an exemplary process of the microscopy aspect of the present invention.
Figure 4B:
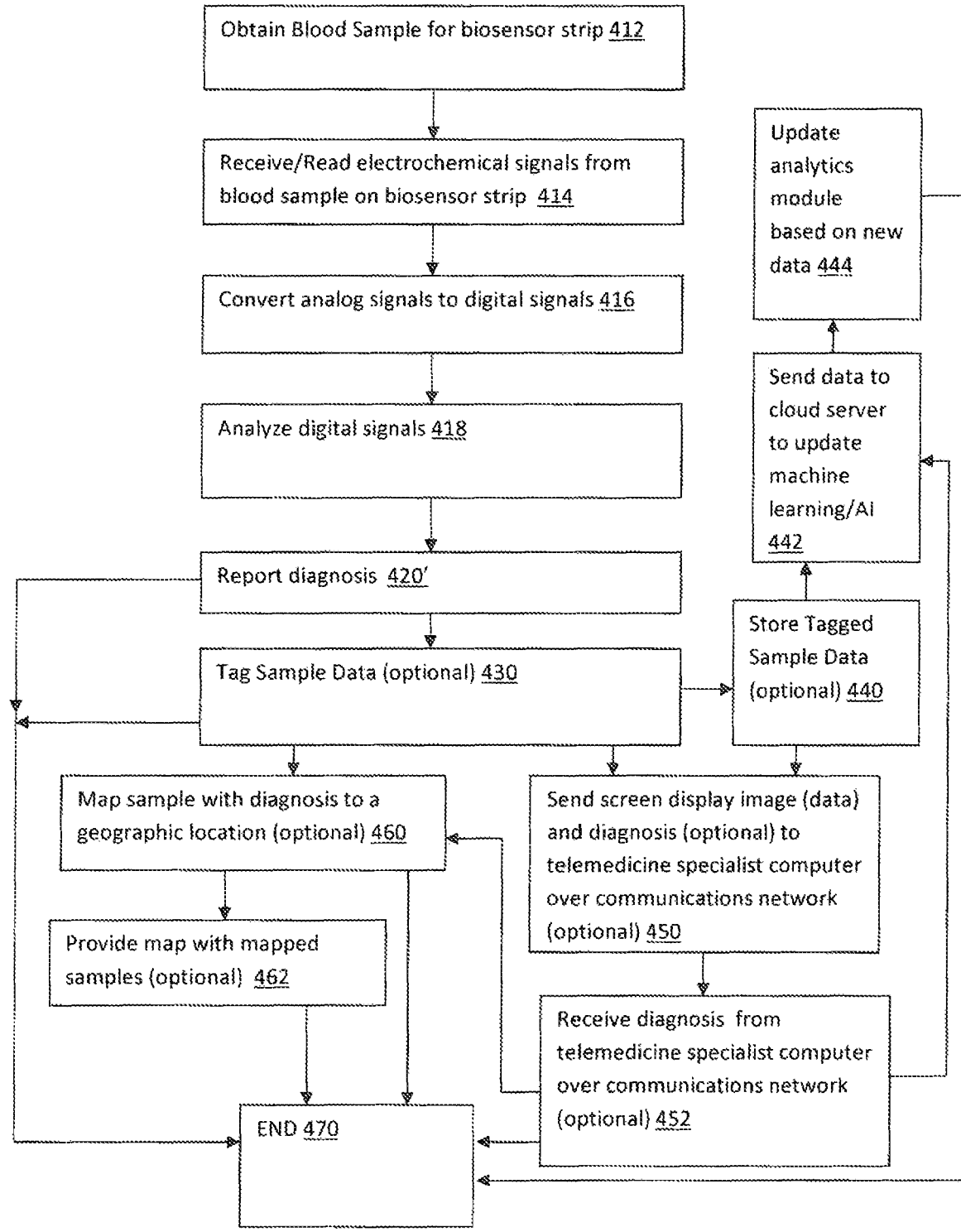
FIG. 4B is a flow diagram for an exemplary process of the electrochemistry aspect of the present invention.

Attention is now directed to FIGS. 4A and 4B, which show flow diagrams detailing computer-implemented processes in accordance with embodiments of the disclosed subject matter. Reference is also made to elements shown in FIGS. 1-3. The process and subprocesses of FIGS. 4A and 4B are computerized processes performed by the system of the invention, and are for example, performed manually, automatically, or a combination thereof, and, for example, in real time.

FIG. 4A is a flow diagram of an example, microscopy process for the microscopy channel of the invention. Initially a blood sample is obtained and placed onto a microfluidic chip, such as microfluidic chip 112, detailed above, and the blood is stained, with the microfluidic chip 112 placed into the base 100, via the port 110, at block 402. Via an optical relay system (optical relay) 214, at block 404, the microscopic image of the blood sample, as stained in the microfluidic chip, reaches the camera 260 of the smart phone or in a standalone device concept 102. The image in the camera/image sensor unit 260 is converted to digital data, e.g., digital signals, at block 406. The digital data is analyzed, at block 408, by the software analysis module 264, by using machine learning and artificial intelligence (AI). The analysis module 264 reports a diagnosis, at block 420. Also, at block 420, the image of the blood sample is displayed on the screen display 103, via screen display module 246. From block 408, the process can move to block 470, where it ends.

Moving to block 430, from block 420, the data for the blood sample, including the visual image can optionally be tagged, by the analytics module 264.

From block 430, the process can move one or more of three optional pathways, defined by block in series 440, series 450 and series 460.

Moving from block 430 to block 440, the tagged sample data can be stored, for example, in the data storage 250. The tagged data can then be sent from the storage, to a cloud server, such as cloud server 270, at block 442, or directly to the cloud server 270, from block 430 to block 442. At block 442, in the cloud server 470, updates its machine learning, artificial intelligence (AI) with the data and diagnosis for the image. The process moves to block 444, where the analytics module 264 is updated with this new data. The process then moves to block 470, where it ends.

Moving from block 430 to block 450, the tagged sample data, or stored tagged sample data (from block 440), in an optional process, can be sent, e.g., transmitted over the network(s) 200 to a telemedicine specialist 280, for example, to his computer 280a or smart phone, tablet computer, laptop computer 280b, and the like. At block 452, a diagnosis is received from the telemedicine provider 280, for example, at the smart phone 102, from where the process moves to block 470 where it ends, or in the cloud server 270. Once in received in the cloud server 270, the process then moves to block 444, where the analytics module 264 is updated with this new data, or to block 460, detailed below. From block 444, the process moves to block 470, where it ends.

At block 460, reached either from block 430, or block 452, the sample, based on a GPS tag and time stamp can be optionally mapped, for example, by the cloud server 270. The process can move to the optional process of block 462, where the cloud server 270 provides a map of all the test results. The process then moves to block 470, where it ends. The process can also move from block 460 to block 470, where it ends.

FIG. 4B is a flow diagram of an example signal processing process for the signal channel of the invention. Initially, at block 412, a blood sample is obtained and placed onto a biosensor strip, such as biosensor strip 116, detailed above. The biosensor strip 116 is placed into the base 100, via the port 114, at block 402. The blood sample causes an electrochemical reaction, which, results in an electrical response being output, at block 414, as an analog signal(s), which is read by the biosensor reader 222. This analog signal output, for example, as amplified by the biosensor reader 222, is input into an analog to digital converter (ADC) 224, at block 416, which converts the analog signals to digital signals. The digital signals are then input into a signal analysis module 226, where the signals are analyzed, at block 418. The signals then pass to the analysis module 264, which reports a diagnosis, at block 420'. Also, at block 420' a graphic and absolute number indicating the state of the G6PD deficiency is displayed on the screen display 103, via screen display module 246. From block 418, the process can move to block 470, where it ends.

From block 420' the process can move to the optional processes of block 430, 440, 442, 444, 450, 452, 460, 462 and ultimately ending at block 470, as detailed above.

Figure 5A:
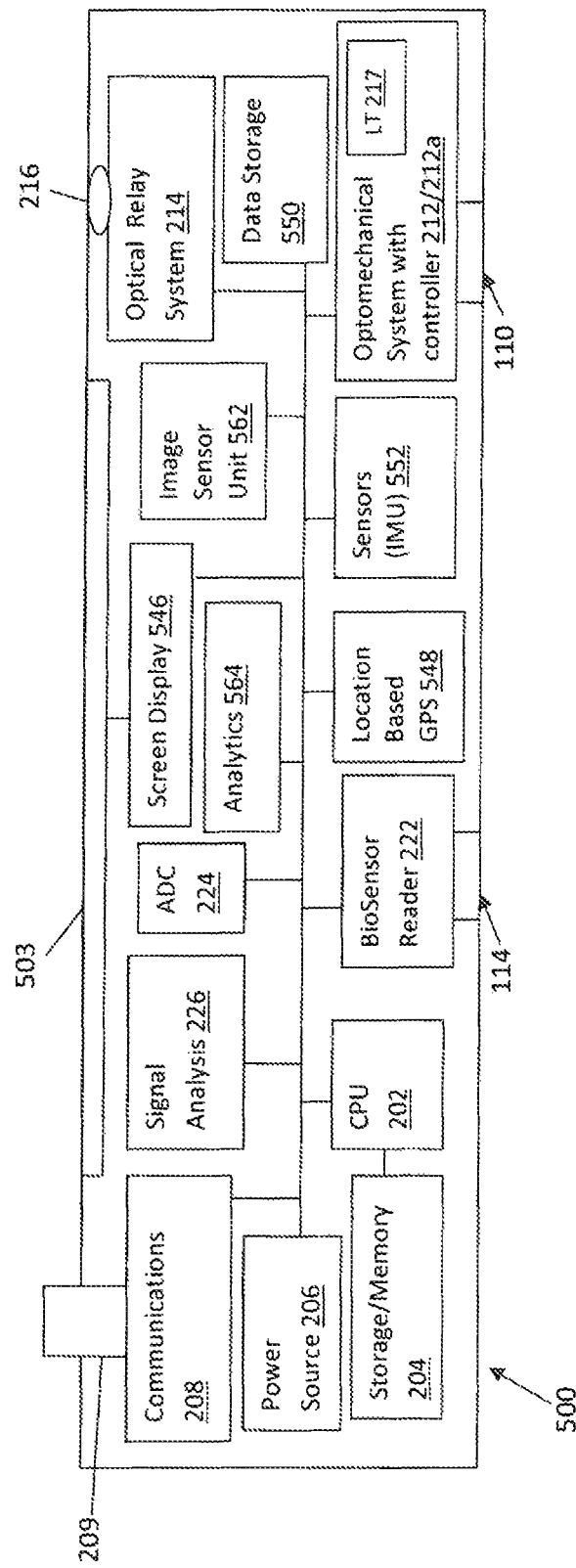
FIG. 5A is a block diagram of a standalone computer device in accordance with embodiments of the invention.
Figure 5B:
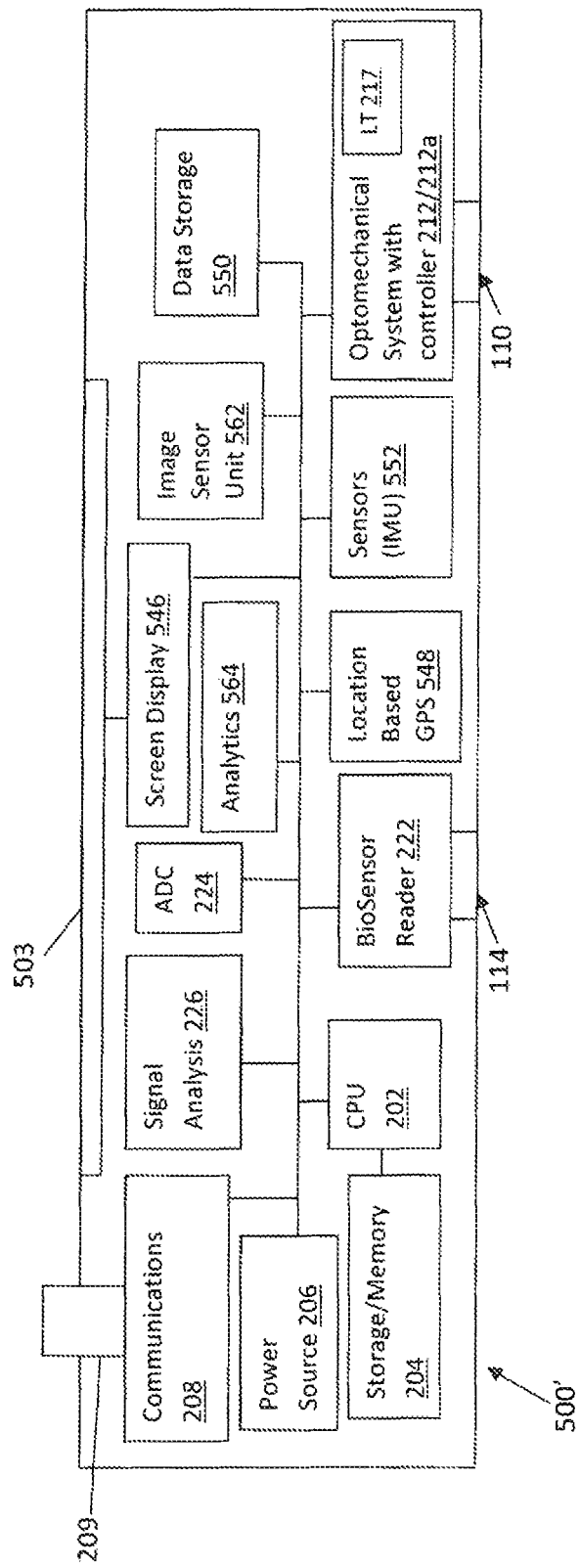
FIG. 5B is a block diagram of another standalone computer device in accordance with embodiments of the invention.

FIGS. 5A and 5B shows alternative mobile computing devices 500, 500' for performing the disclosed processes via a microscopy channel and a signal channel. The devices 500, 500' include components identical or similar to those in device 100, and have the same element numbers, and are in accordance with that described above for the device 100 of FIG. 2. Components, including the screen display module 546 (which controls the screen display 503, e.g., a touch screen, of the device 500), location based GPS module 548, data storage 550, sensors IMU 552, image sensor unit 562 and analytics module 564, are identical or similar to the corresponding components on the smart phone 102 of FIG. 2, but have element numbers in the 500's (rather than the 200's in FIG. 2), and are in accordance with the correspondingly numbered component in FIG. 2. The analytics module 564 analyzes the scanned sample, for example, by image identification, Artificial Intelligence and the like, to determine the existence or nonexistence of a disease and/or condition (e.g., diagnosis of malaria parasites), or a measurement (for example, blood glucose levels and complete blood cell counts). The optical relay system 214 is optional, as the device 500 (FIG. 5A) can work as a standalone device, where the lens 216 and the optical relay system 214 are not needed, or with a smart phone or other device, where the optical relay system 214 and lens 216 may be needed. The device 500' (FIG. 5B) lacks the optical relay system 214 and the lens 216, and as such, operates exclusively as a stand-alone device.

Figure 5C:
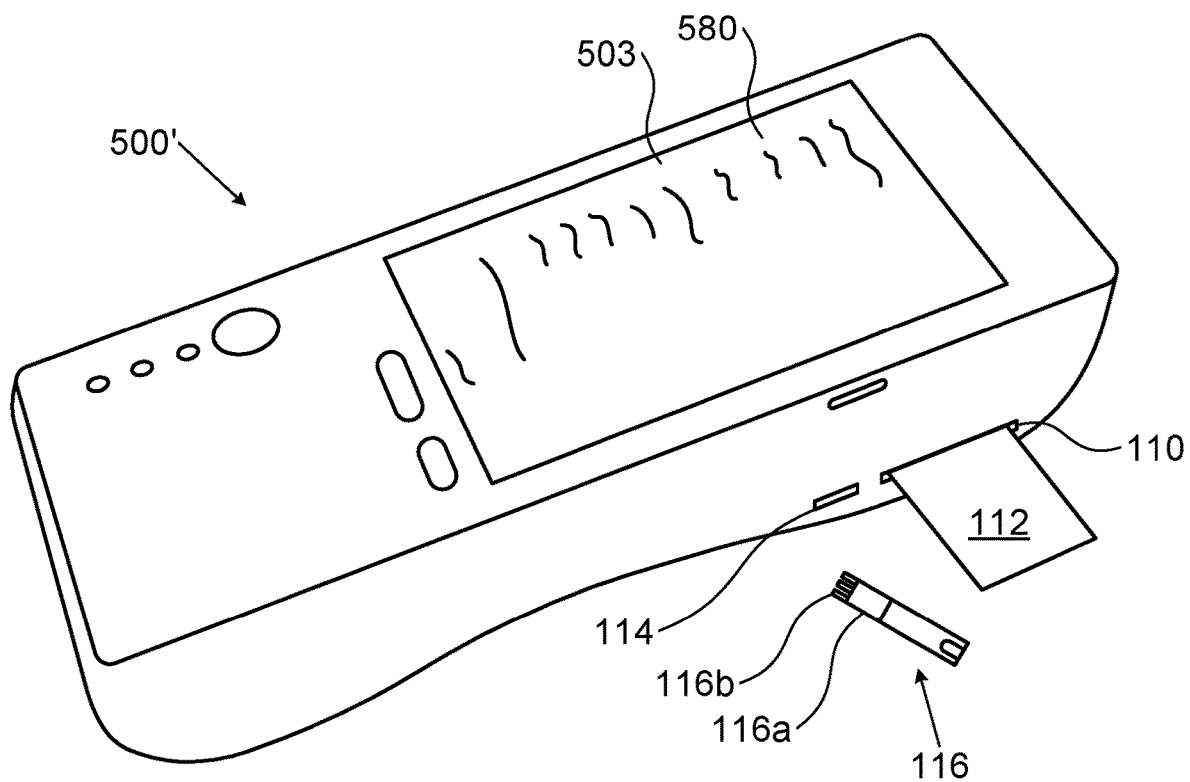
FIG. 5C is a perspective view of the device of FIG. 5B.

FIG. 5C shows the device 500' as a stand-alone unit, including a screen display 503, which is presenting a screen shot 580. This device 500' is hand held and therefore portable and battery operated as well as option for recharging from external power supply and solar energy.

FIG. 7 shows a process as a decision diagram, for example, programmed into (and performed by) the CPU 202 of devices 100, 500, and 500' for treatment decision support (e.g., providing treatment recommendations, treatment protocols and the like). The treatment recommendations and protocols appear for example, as user interfaces (UI) on screen displays, such as those on the screen display 503 of the stand-alone device 500', shown as screen displays (screen shots) 580*a*-580*d* in FIGS. 8A-8D, and detailed below.

In a first branch of the process, if *Falciparum* malaria is detected, at block 702. A glucose check is performed to see if the subject is hypoglycemic, at block 704. If yes, a treatment with artemisinin combination therapy (ACT) is suggested, at block 706. At block 708, if primaquine is used for prevention of a further transmission, G6PD deficiency testing, via devices 100, 500, 500' disclosed herein, may be used before treatment.

In a second branch of the process, if Non-*Falciparum* malaria or mixed infection is detected, at block 712. Treatment is suggested with ACT or chloroquine as well as G6PD testing via devices disclosed 100, 500, 500' herein, at block 714. If G6PD is negative, treatment with primaquine is suggested, at block 716.

In a third branch of the process, should there be a negative test for *Falciparum* and Non-*Falciparum* malaria, testing with the devices 100, 500, 500' as disclosed above, is suggested to be performed if the patient has high clinical suspicion, at block 722.

Figures 8A, 8B:
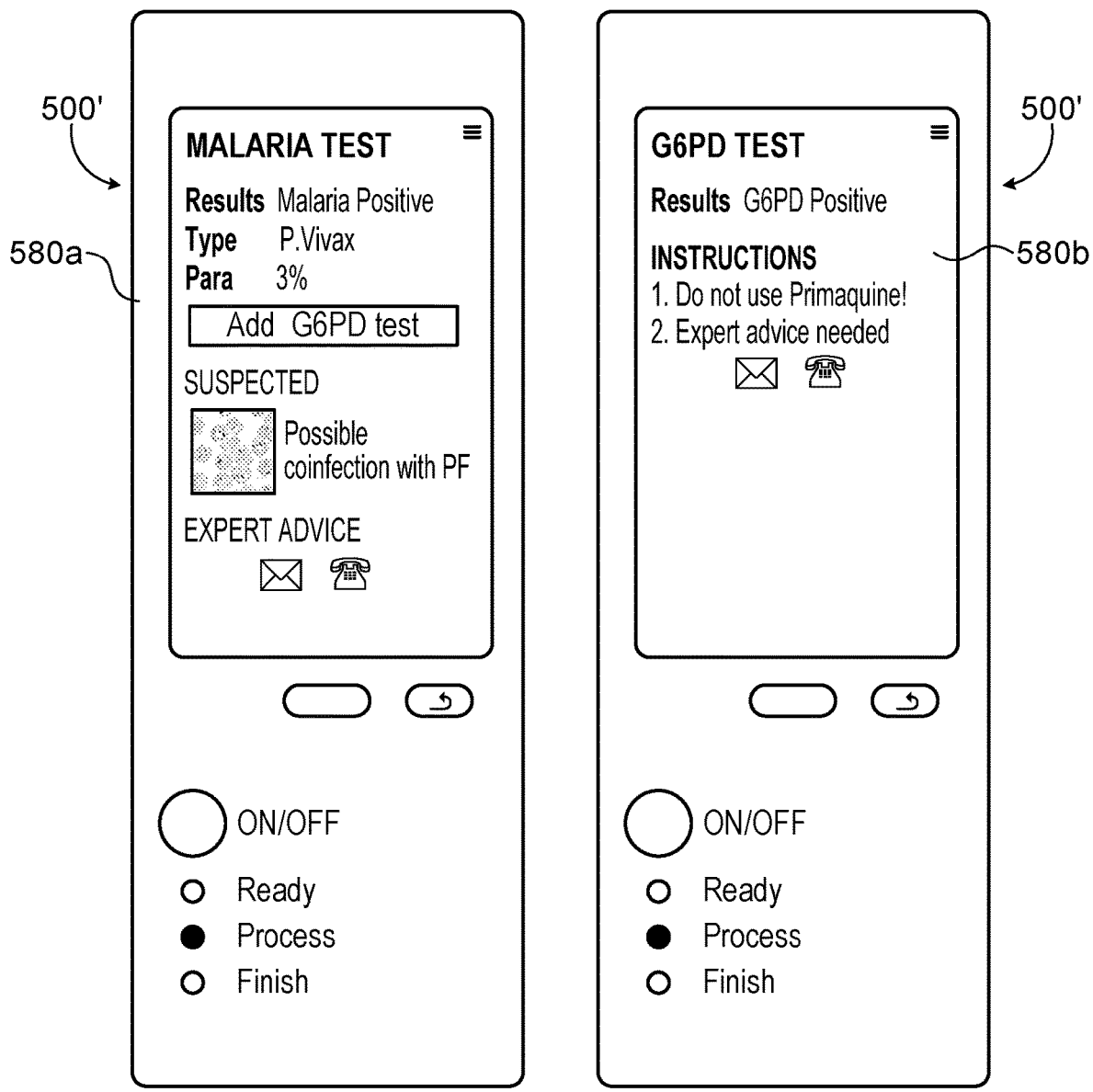
Figure 8C:
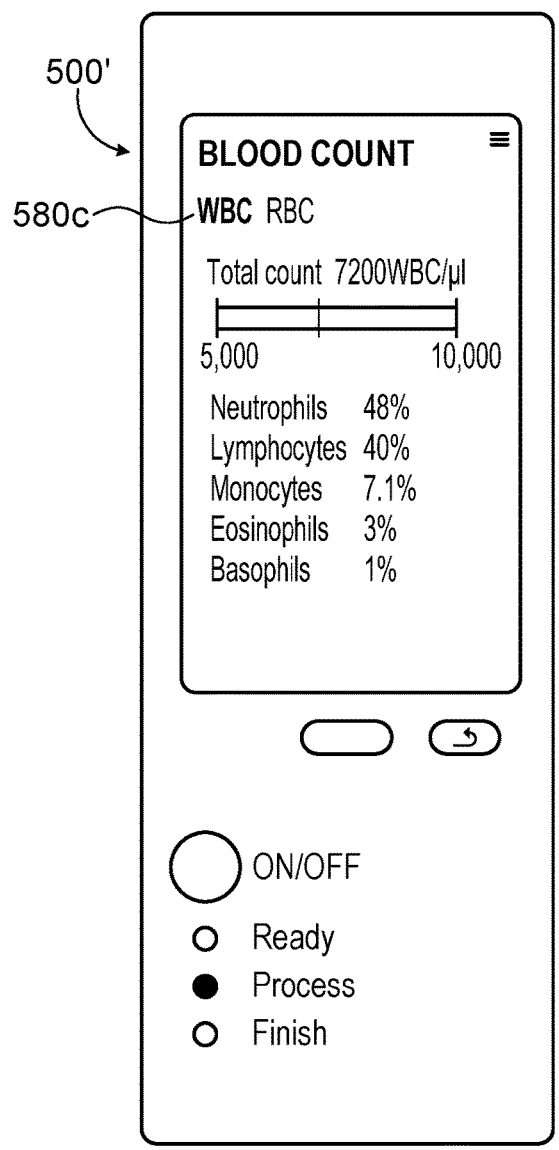
Figure 8D:
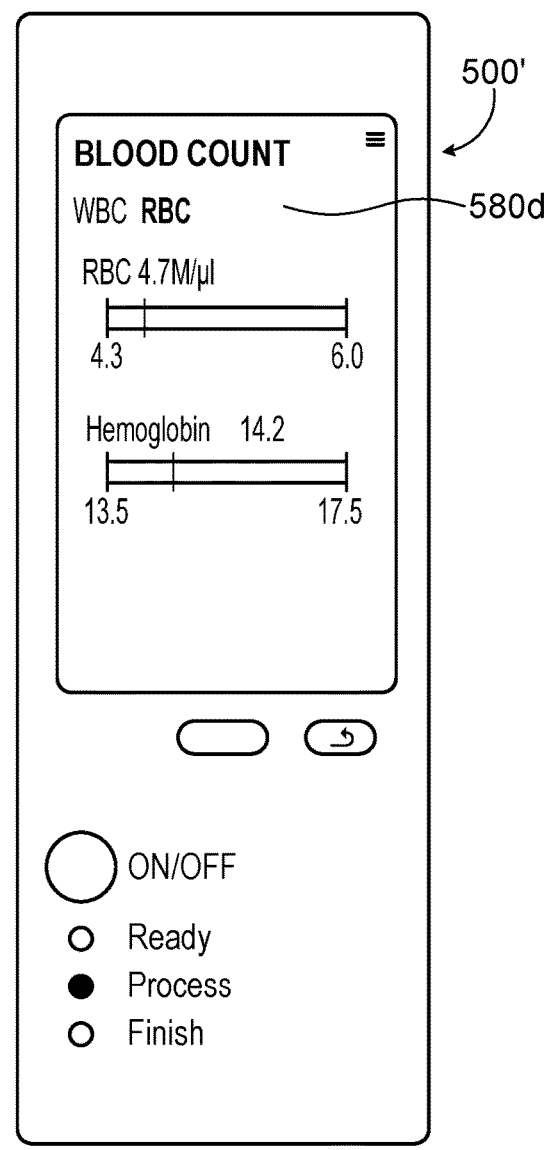

FIG. 8A shows the device 500' with a screen shot 580*a* showing the result of a malaria test, and suggesting a treatment protocol. FIG. 8B shows the device 500' with a screen shot 580*b* showing the result of a malaria test, and providing information on medicines, which could be from the CPU 202 or a cloud server 270. FIG. 8C shows the device 500' with a screen shot 580*c* detailing a white blood cell count. FIG. 8D shows the device 500' with a screen shot 580*d* detailing a red blood cell count.

While the devices and methods disclosed above relate to diseases, such as malaria, these devices are also adaptable for diagnosing other diseases conditions and blood count such as white/red blood cell counts and white blood cell differentiation, with various modules programmed to recognize white/red blood cells and for analytics thereof.

The implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, non-transitory storage media such as a magnetic hard-disk and/or removable media, for storing instructions and/or data. Optionally, a network connection is provided as well. A display and/or a user input device such as a keyboard or mouse or printer are optionally provided as well.

For example, any combination of one or more non-transitory computer readable (storage) medium(s) may be utilized in accordance with the above-listed embodiments of the present invention. The non-transitory computer readable (storage) medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

As will be understood with reference to the paragraphs and the referenced drawings, provided above, various embodiments of computer-implemented methods are provided herein, some of which can be performed by various embodiments of apparatuses and systems described herein and some of which can be performed according to instructions stored in non-transitory computer-readable storage media described herein. Still, some embodiments of computer-implemented methods provided herein can be performed by other apparatuses or systems and can be performed according to instructions stored in computer-readable storage media other than that described herein, as will become apparent to those having skill in the art with reference to the embodiments described herein. Any reference to systems and computer-readable storage media with respect to the following computer-implemented methods is provided for explanatory purposes, and is not intended to limit any of such systems and any of such non-transitory computer-readable storage media with regard to embodiments of computer-implemented methods described above. Likewise, any reference to the following computer-implemented methods with respect to systems and computer-readable storage media is provided for explanatory purposes, and is not intended to limit any of such computer-implemented methods disclosed herein.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As used herein, the singular form "a", "an" and "the" include plural references unless the context clearly dictates otherwise.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The above-described processes including portions thereof can be performed by software, hardware and combinations thereof. These processes and portions thereof can be performed by computers, computer-type devices, workstations, processors, micro-processors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A dual channel diagnostic device comprising:
an imaging channel comprising:
a first port for providing the diagnostic device with a first sample;
an optical system for rendering the first sample as an image viewable on a display;
an imager for obtaining an image of the first sample from the optical system; and
an analytics module configured for analyzing the image of the first sample and providing a diagnosis including a determination of one of: a first disease condition or test result, from the image; and,
a signal channel comprising:
a second port for providing the diagnostic device with a second sample;
a signal generator in communication with an electrochemical sensor for converting an electrochemical response from the electrochemical sensor from an electrode having reacted with the second sample; and
a signal analyzer for analyzing received signals from the signal generator, to providee a diagnosis including the determination of one of: a second disease condition or test result;
wherein a disease condition or test result is determined from one or both of the first disease condition or test result and the second disease condition or test result.

2. The device of claim 1, wherein the analytics module is configured for the providing of the diagnosis, from the image, 1) for a disease condition including: anemia, malaria parasites including, P. falciparum, P. vivax, P. malaria. P. ovale, P. knowlesi and the disease stage, multi-parasites including relapsing fever and Filarias, Tuberculosis, and, veterinary diseases, and 2) for a test result including: blood count, malaria parasites including, P. falciparum, P. vivax, P. malaria. P. ovale, P. knowlesi, complete blood cell counts, Pap smear analysis, multi-parasites, and urine tests.

3. The device of claim 1, wherein the microscopy system includes an optomechanical system for magnifying the first sample.

4. The device of claim 1, additionally comprising: a processor programmed to determine a treatment for the provided diagnosed disease condition or the test result, the processor in communication with the analytics module.

5. The device of claim 1, additionally comprising: a processor programmed to determine a treatment for the provided diagnosed disease condition or the test result, the processor in communication with the analytics module and the signal analyzer.

6. The device of claim 1, wherein the imaging channel and the signal channel are configured to output the provided diagnosed disease condition or the test result in real time.

7. The device of claim 1, additionally comprising: a display in communication with the imaging channel and the signal channel, the display comprising: 1) a screen display, and/or, 2) a display output configured for communicating with an image sensor of an external computer device for displaying graphics on the display screen of the external computer device.

8. The device of claim 7, wherein the imaging channel includes a first end including the first port, and an oppositely disposed second end associated with the display.

9. The device of claim 7, additionally comprising a processor programmed to transmit data to the display which causes presentation of a User Interface (UI) graphic display of the presence of the diagnosed disease condition.

10. The device of claim 1, additionally comprising:
an analog to digital signal converter (ADC) in communication with the signal analyzer; and,
a signal reader in communication with the electrochemical sensor for reading electrochemical signals emitted from the electrode having reacted with the second sample, the signal reader in communication with the ADC.

11. The device of claim 10, wherein the signal analyzer is configured for analyzing signals to provide the diagnosed disease condition or the test result selected from the group comprising: G6PD output, and blood glucose levels, malaria parasites including, P. falciparum, P. vivax, P. malaria. P. ovale, P. knowlesi and the disease stage, complete blood cell counts, multi-parasites including: relapsing fever and Filarias, Tuberculosis, Pap smear analysis, and veterinary diseases.

12. The device of claim 1, additionally comprising: a location module in communication with at least one of the imaging channel or the signal channel, the location module configured for displaying real- time location indications based on Global Positioning System (GPS) mapping of the diagnosed disease condition or the test result.

13. The device of claim 1, additionally comprising: a microfluidic chip for holding the first sample, the microfluidic chip n for receipt in the first port.

14. The device of claim 13, wherein the microfluidic chip is configured for mixing the first sample with one or more staining agents, imaging enhancers, and dilutants.

15. The device of claim 1, additionally comprising: a biosensor strip including an electrode for producing an electrochemical response when contacted by the second sample, for receipt in the second port.

16. The device of claim 1, where the first disease condition or test result and the second disease or test result are the same disease condition or test result.

17. The device of claim 1, where the first disease condition or test result and the second disease or test result are a different disease condition or test result.

18. The device of claim 1, wherein the imager comprises at least one of: a camera, a scanner, and one or more image sensors.

19. The device of claim 1, wherein the first sample and the second sample are from a same source comprising at least one of: tissue, blood, urine, sputum, and bodily fluid.

20. A method for analyzing tissue samples comprising:
providing a first sample to an imaging channel of a dual channel diagnostic device via a first port;
with the first sample in the imaging channel:
rendering the first sample as an image viewable on a display;
obtaining an image of the first sample;
analyzing the image of the first sample, and,
providing a diagnosis including a determination of one of: a first disease condition or test result, from the image;
providing a second sample to a signal channel of the dual channel diagnostic device; and
with the second sample in the signal channel:
generating signals corresponding to an electrochemical response received by an electrochemical sensor from an electrode having reacted with the second sample;
analyzing the generated signals to provide a diagnosis including the determination of one of: a second disease condition or test result; and
determining a diagnosis comprising a disease condition or test result from one or both of the first disease condition or test result and the second disease condition or test result.

21. The method of claim 20, wherein information as to the determined diagnosis is outputted to the display.

22. The method of claim 20, wherein the first sample and the second sample include portions of the same sample which comprises at least one of blood, urine, and tissue.

23. The method of claim 20, wherein the first disease condition or test result and the second disease condition or test result are either: 1) the same disease condition or test result, or 2) a different disease condition or test result.

* * * * *